United States Patent [19]

Brinkmann et al.

[11] Patent Number: 4,518,357
[45] Date of Patent: May 21, 1985

[54] FASTENING SYSTEM FOR MUCOUS MEMBRANE-SUPPORTED DENTURE

[75] Inventors: Egon Brinkmann; Mandred Putenat, both of Oldenburg; Erhard Dörre, Plochingen, all of Fed. Rep. of Germany

[73] Assignee: Fedlmühle Aktiengesellschaft, Düsseldorf, Fed. Rep. of Germany

[21] Appl. No.: 440,741

[22] Filed: Nov. 10, 1982

[30] Foreign Application Priority Data

Nov. 14, 1981 [DE] Fed. Rep. of Germany ....... 3145260
Oct. 7, 1982 [DE] Fed. Rep. of Germany ....... 3227174

[51] Int. Cl.³ .............................................. A61C 8/00
[52] U.S. Cl. .................................... 433/173; 433/177
[58] Field of Search ........................ 433/173, 177, 176

[56] References Cited
U.S. PATENT DOCUMENTS

1,101,810 6/1914 Otrich et al. ....................... 433/177

Primary Examiner—Robert Peshock
Attorney, Agent, or Firm—Toren, McGeady, Stanger

[57] ABSTRACT

A fastening system for a mucous membrane-supported denture is composed of a removable, mucous membrane-supported denture (3) and holding devices which effect a secure support during the wearing of the denture. The holding devices are composed of two greater than hemispherical heads (1) arranged either on natural teeth or on implants. The ball heads (1) are engaged in retaining caps (8) fastened in recesses (7) of the denture (3), the caps being composed of smooth, elastic plastic which contact the ball heads (1) only in the area of their equators M. Adapting rings (12) composed of a plastic material which is more elastic than that of the retaining caps (8) are arranged in the area of the openings (9) of the retaining caps (8) and effect a uniform contact of the retaining caps (8) on the ball heads (1). As a result, a secure support of the denture is achieved without a rigid connection between the ball heads (1) and the denture (3).

14 Claims, 8 Drawing Figures

FASTENING SYSTEM FOR MUCOUS MEMBRANE-SUPPORTED DENTURE

BACKGROUND OF THE INVENTION

1. Field of the Invention

The present invention is directed to a fastening system for a mucous membrane-supported denture composed of ball or spherical heads fastened from implants or natural teeth. The size of the head is greater than a hemisphere and the surface is highly polished surface. The head secures the denture and engages the retaining caps provided in recesses of the denture which are composed of smooth and elastic plastic material.

2. Field of the Invention

Dentures which adhere by means of suction action on the palate or which are supported by means of gripping elements on the remainder of the tooth are known. These dentures can be designated as mucous membrane-supported dentures. The latter are often unsatisfactorily supported and loosen during the intake of food and when talking. Therefore, the fastening of an artificial tooth substitute on enossal implants inserted in the ridge of the jaw has been suggested. This technique is widespread in dentistry but cannot be applied successfully in every case. Rather, it is substantially restricted to providing a secure support to individual tooth substitutes which cannot be removed or to abridged rows of teeth and is employed for this purpose with some success.

Patent CH No. 597,843 discloses a system for fastening a mucous membrane-supported denture in which a denture, having a retaining cap made of an elastic material attached, is fastened on implants carrying spherical heads. The retaining caps encircle or encase the spherical heads almost completely, thereby producing a rigid fastening of the snap fastener type. However, this system is disadvantageous because a lateral movement of the denture is not possible due to the rigidity of the support.

Patent FR No. 12 11 044 discloses the fastening of spheres or cylinders made of rust free, non-magnetic metals or alloys on screw-shaped implants. The suggested cylindrical form provides for a ball cap on the end by which the cylinder is fastened on the implant. Correspondingly formed matching pieces, so-called male molds, are provided for fastening on the spheres or cylinders. The matching pieces are welded together by means of metal bands, resulting in a rigid connection to produce a removable bridge. Special rod-like pieces fastened to the matching pieces are slid over the spheres or cylinders or the end plate of the matching piece serve for the fastening of the tooth substitute. A disadvantage in this system is that the forces occurring during chewing are transmitted directly to the sphere head or the implant as a consequence of the rigid connection. A further suggestion in FR No. 12 11 044 provides for an elastic substance arranged in the matching pieces. However, this embodiment is also disadvantageous since a lateral movement of the tooth substitute is not possible due to the rigidity of the connection.

U.S. Pat. No. 1,101,810 describes a fastening system which also has the disadvantage that a lateral movement of the mucous membrane-supported denture is not possible. In this older suggestion, a sphere-shaped spring clip is embedded in the denture and covers a full sphere fastened in a tooth root by a pin. A further disadvantage of the full sphere is that the sphere projects far into the mouth cavity and the denture therefore has a greater tilting gradient. A further disadvantage, as in other prior art disclosures, is that a closure of an opening arranged in the jaw is not possible with a full sphere and, e.g., an end plate must be employed for closing a tooth root opening.

It has also been attempted to provide improved supports for removable tooth substitutes, such as, e.g., lower jaw dentures, with the help of implants or links inserted in the jaw ridge, the removable tooth substitutes being fastened on round or angular implant posts projecting from the jaw ridge. However, these attempts were not too successful, in particular, in the treatment of toothless lower jaws. The reasons for this are as follows: As a consequence of advanced atrophy in the lateral portion of the jaw bone, extremely unpleasant anatomical relations arise so that the insertion of implants in this area is seldom considered. Consequently, it is primarily the regio interforaminalis of the lower jaw that is available for implantations. When implants inserted in this area and connected with links are employed for supporting a lower jaw denture, a more or less rigid connection results.

Due to the resiliency of the lateral mucous membrane, a constant tilting load occurs during chewing and talking. The higher the implant posts project from the jaw bone, the more the tilting load increases. Consequently, the denture is not sufficiently secure and the denture wearer has a constant feeling of insecurity. This is because in the phase of the last closing movement, the lower jaw, as is known, carries out a vertical and horizontal movement which ends in a rotational movement. The previously known implantation systems or the removable tooth substitute attached to the implant, respectively, could not follow this movement without a defective loading occurring, in particular, with divergently inserted implant posts.

SUMMARY OF THE INVENTION

We have discovered a novel fastening system for a removable, mucous membrane-supported denture which eliminates the existing disadvantages of known fasteners, and by means of which, the denture, particularly for the total tooth substitute of the lower jaw, obtains a firm support which is secure relative to laterally acting forces. In particular, to avoid the above outlined disadvantages, the denture should not be connected with the implants by means of a rigid connection, but rather, should be movable in a certain manner during the chewing process.

The present invention achieves an optimum support of a mucous membrane-supported denture during small as well as extreme lateral and vertical movements of the jaw. In addition, the present invention avoids the known disadvantages which result in the use of metal parts in the mouth cavity.

Finally, the invention also provides secure support for a denture even if this denture must be fastened on implant posts which are arranged divergently.

More particularly, the present invention provides a fastening system for a removable, mucous membrane-supported denture which is composed of spherical heads for fastening the denture, which heads are fastened on implants or natural teeth. The heads are larger than a hemispheroid and have a highly polished surface. Retaining caps provided for engagement with the heads are fastened in recesses of the denture and are composed of smooth and elastic plastic material. The mucous membrane-supported denture has two retaining caps provided for engagement with two spherical heads and are adapted so that the caps contact the spherical heads only in the area of their equators, i.e., area of widest cross-sectional area. Adapting rings of a plastic material which is more elastic than the material of the retaining caps are arranged between the walls of the recesses and the retaining caps near or at the opening of the retaining caps, i.e., the area of contact between the heads and the retaining caps, so that the retaining caps are spaced apart from the wall of the recess.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

BRIEF DESCRIPTION OF THE DRAWINGS

FIG. 1a is a schematic section according to line Ia—Ia of FIG. 1b showing a lower jaw denture with two spherical heads in retaining caps.

FIG. 1b is an embodiment example of the fastening system according to the invention, shown in the partial view of a lower jaw denture with a retaining cap, adapting ring and a spherical head, sectioned on the plane Ib—Ib of FIG. 1a.

FIGS. 5a and 5b depict the cooperation of the tooth substitute system with implants inserted divergently, through the example of a lower jaw denture before and after the final assembly, sectioned on line V—V of FIG. 1a;

DESCRIPTION OF THE PREFERRED EMBODIMENT

Figures 1A, 1B:
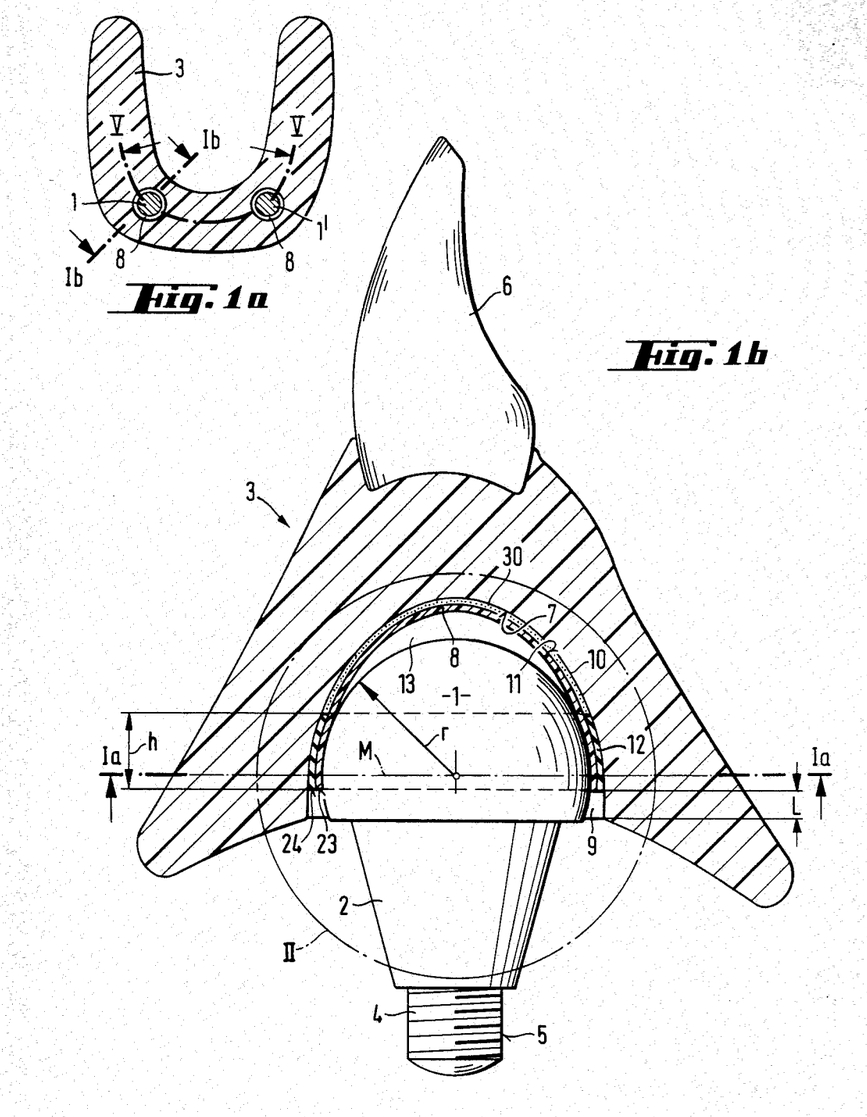
Figure 6:
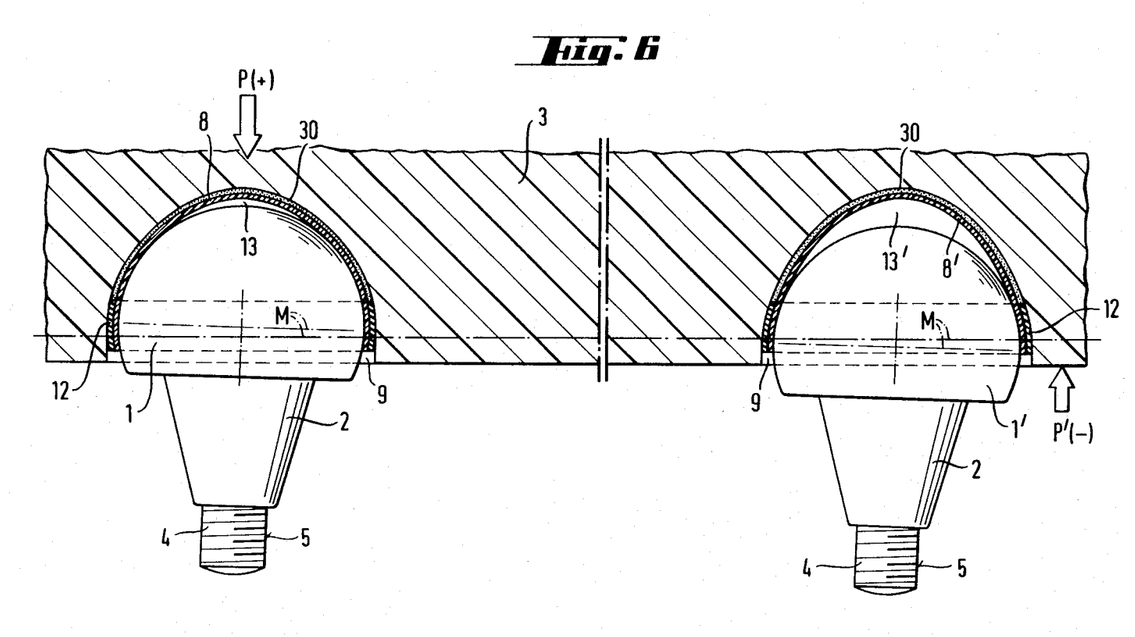
FIG. 6 depicts the functioning of the tooth substitute system, according to the invention, shown in simplified form through the example of a lower jaw denture loaded on one side.

Referring to the drawings, FIG. 1b shows a partial view of the fastening system according to the invention shown through the example of a lower jaw denture. The entire system is composed of a lower jaw denture 3 for the total tooth substitute and two ball or sphere heads 1 provided for the fastening of the lower jaw denture 3. Only one of the ball heads 1 is shown in FIG. 1b. Ball head 1, composed of densesintered aluminum oxide with a purity of 97.5 weight percent and a RMS value of $R_a = 0.03$, which is attached on a pin-formed projection 2 and on whose lower end 4 is cut in a thread 5, is constructed to be larger than a half ball shape, i.e., greater than hemispherical, and its volume amounts to 78.4% of the full ball volume. An artificial tooth 6 is fastened on the lower jaw denture 3. A retaining cap 8 produced from polyvinyl chloride is located in the recess 7 of the lower jaw denture 3, which retaining cap 8 is fastened in this place with a plastic 30 which can be cold-polymerized. Retaining cap 8 contacts the ball head 1 in the area of its equator M, i.e., greatest circumference. In the opening area 9 of the recess 7, between the wall 10 of the recess 7 and the inner wall 11 of the retaining cap 8, is adapting ring 12 made from polyethylene vinyl acetate which, as will be shown hereinbelow in FIG. 6, provides for an exact contact of the retaining cap 8 when lower jaw denture 3 changes position and, as a consequence of which, a consistent and constant friction is effected between the ball head 1 and retaining cap 8.

Figure 2:
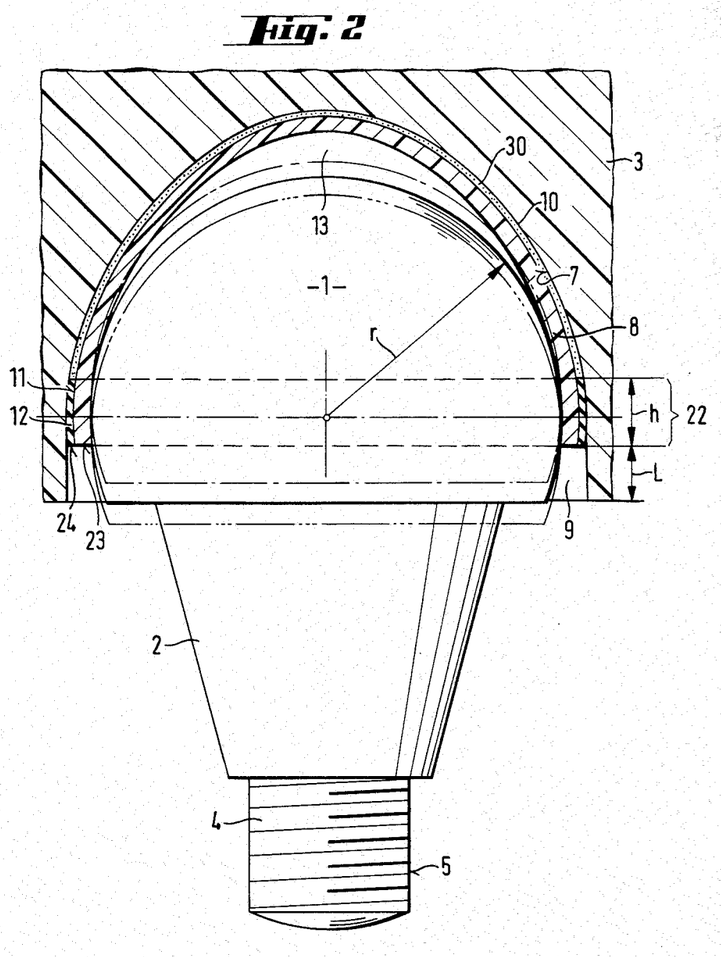
FIG. 2 is an enlarged partial view of area II of FIG. 1b showing the retaining cap and adapting ring.

As can be understood from FIG. 2, the retaining cap 8 is constructed in such a way that it contacts the ball head 1 only in its equator area while a hollow space 13 remains open in its upper area. The ball head 1 can penetrate into this area during non-uniform loading. In the embodiment form shown in FIG. 2, retaining cap 8 and adapting ring 12 form a flush closure with one another with their lower edges 23 and 24. The adapting ring 12 is constructed in such a way that the relation of its height h to radius r of the ball head 1 is 1.5:2.5.

Figure 3:
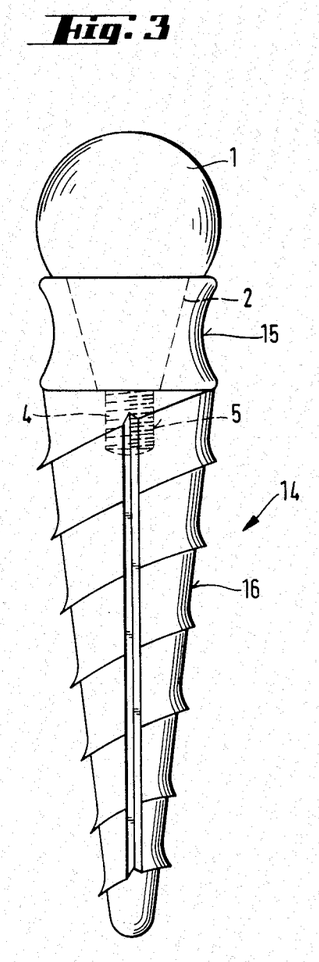
FIG. 3 is a spherical head according to the invention fastened on a pin implant provided with a thread.

A ball head 1 is shown in FIG. 3 which is fastened with a pin-shaped projection 2 having a thread 5 on its lower end 4, on a screw-shaped implant 14 composed of densely sintered aluminum oxide which has a thread 16 on its outer side. Screwing in tools can be applied in a force-locking manner on the ball head 1. The implant 14 has a concave area 15 for arranging the epithelial sleeve.

Figure 4:
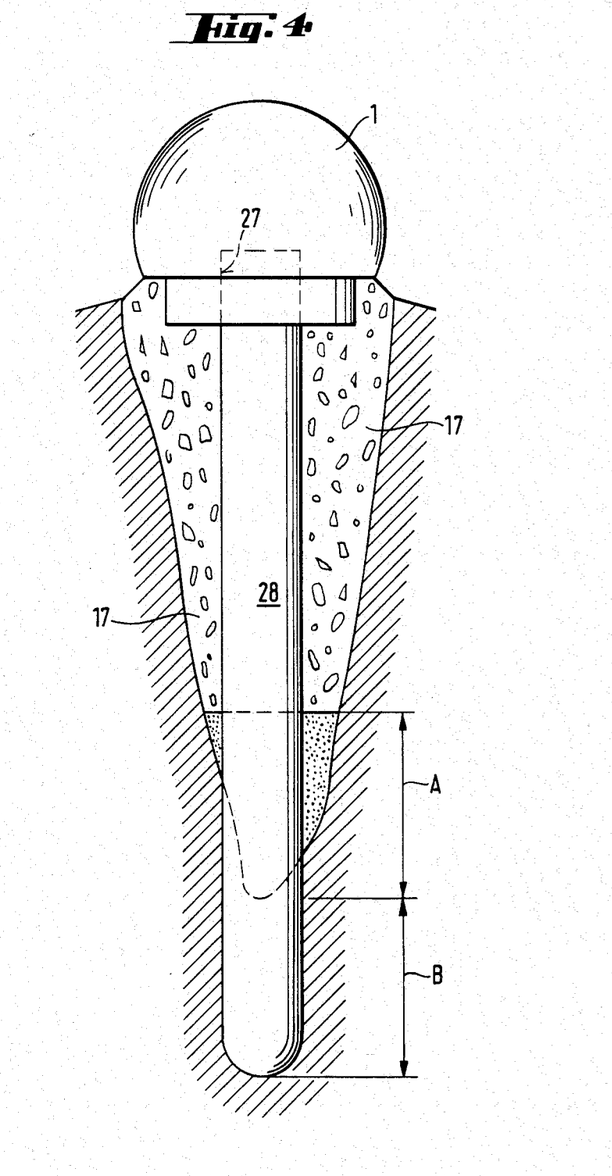
FIG. 4 is a spherical head fastened in a natural tooth.

FIG. 4 shows a ball head 1 which is anchored with its pin 28 in a natural tooth root 17. The pin 28 is constructed cylindrically and is fastened in the recess 27 of the ball head 1 by means of cement, not shown. When inserting the ball head 1 with its pin 28, in the natural tooth root 17, the tooth will first be pulled in a manner known per se and the tooth root will be shortened by a measurement A. The alveolus is deepened by measurement B and the pin 28 is adapted to the tooth root 17 or the deepened alveolus. This is effected by means of cutting off the end of the pin 28 to be connected with the ball head 1. The cementing of the pin 28 is effected with cement in the natural tooth root 17.

Figure 5A:
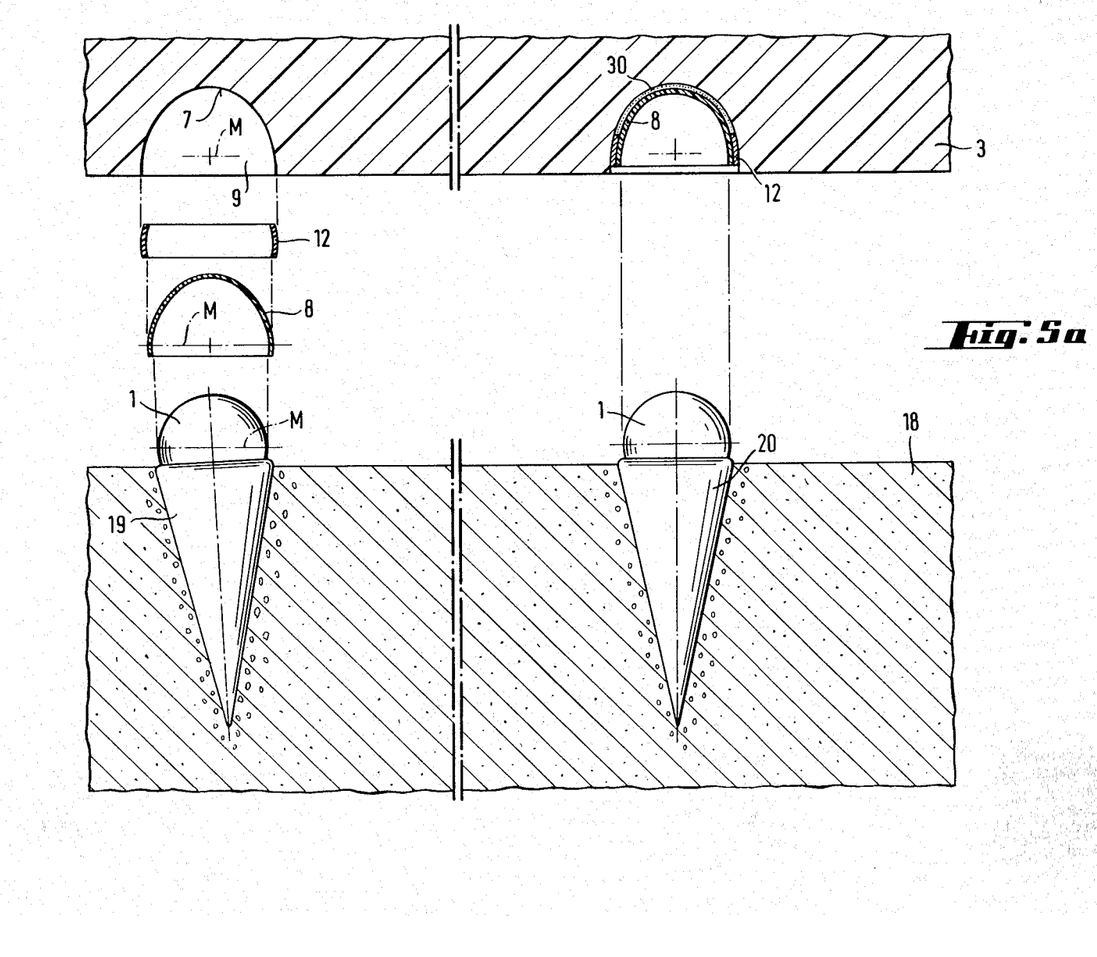
Figure 5B:
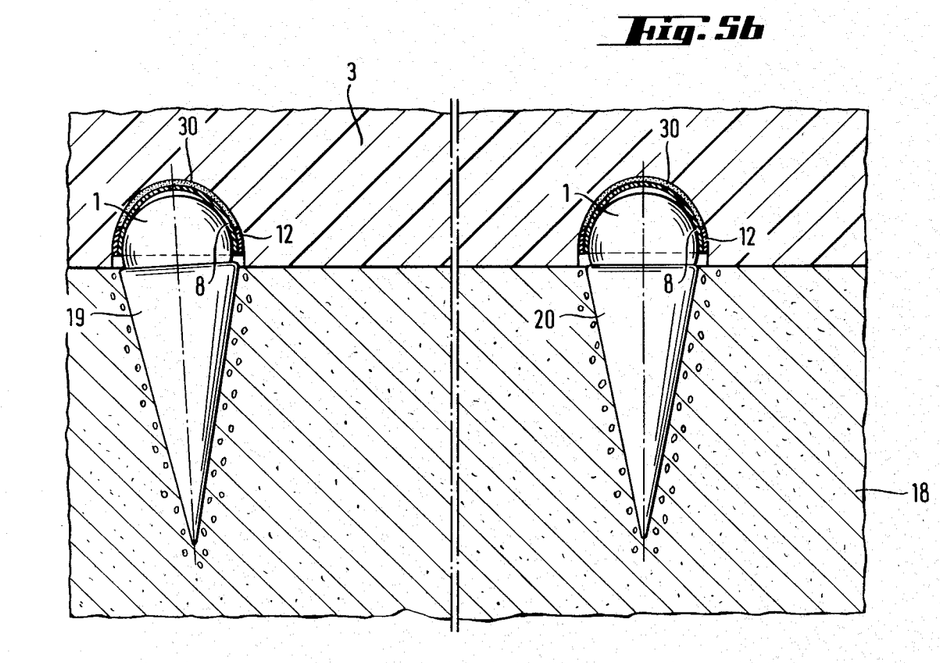

FIGS. 5a and 5b show two implants 19 and 20 inserted divergently in the lower jaw 18. To facilitate understanding, the lower jaw denture 3 is shown lifted up from the retaining cap 8 in FIG. 5a. The figures show that in spite of divergent insertion of implants 19 and 20, the full ability of the tooth substitute system to function is ensured. In particular, FIG. 5b shows (at left), how ball head 1 and retaining caps 8 effect a compensation in an assembled tooth substitute system with obliquely inserted implants.

FIG. 6 shows the functioning of the fastening system according to the invention during one-sided loading. By means of the construction of the retaining cap 8 with the hollow space 13, it is possible that the lower jaw denture 3 with the retaining caps 8 will be pressed more strongly into the ball head 1 during a strong load P(+). At the same time, the hollow space 13' enlarges by means of the load release occurring there P' (—) without the denture supported on the ball head 1' by means of the retaining cap 8' losing its secure support which is sealed by means of the adapting ring 12 enclosing the retaining cap 8'.

By using only two spherical heads for fastening the mucous membrane-supported denture and since the retaining caps of the denture contact the ball heads only in the area of their equators, there is a secure support of the denture without a rigid connection between the ball heads and the denture. Such a rigid connection exists in the system described in CH No. 597,843 where, because of the almost complete enclosure of the ball head by means of the retaining caps arranged in the denture, essentially all mobility is prohibited.

The excellent support of the denture during vertical and lateral movements of the jaw results due to the use of a plastic material of higher elasticity than that of the retaining caps for the adapting rings. The adapting rings arranged in the area of the openings of the retaining caps between the walls of the recesses for the retaining caps and the retaining caps enclose the retaining caps and effect their close contact on the ball heads.

When one of the two retaining caps presses deeper into the ball head during one-sided chewing pressure, the other retaining cap necessarily undergoes an opposing movement. During this process, the retaining caps glide over alternating diameters of the ball heads. As a consequence of their high elasticity, the adapting rings effect a pressure acting in the radial direction on the retaining caps, thereby effecting a close contact of the retaining caps with the ball heads during their up and down movement and without the concomitant up and down movement either of the retaining caps or of the denture being impaired in any way. In a similar way, the adapting rings also effect a close contact of the retaining caps during laterally acting loads.

Accordingly, the present invention has provided a fastening system in which a denture supported with the help of implants, and in particular, divergently inserted implants, can follow the chewing movement of a lower jaw ending in a rotational movement, without misloading and thus loosening of the implants being brought about.

Although the fastening system according to the invention results in a concomitant albeit minimal movement of the denture, at no time does the feeling of insecurity arise for the denture wearer. A further advantage of the fastening system according to the invention is that it provides for compensation of the resiliency of the mucous membrane since the denture does not press continuously on the mucous membrane, in contrast to the previously known fastening systems.

It is also possible with the present invention, to dispense with the link connections between the individual implant posts which were often employed when an additional securing of the denture was desired. The disadvantage of this web construction was that it could exert a certain lifting effect on the adjacent implant posts and, due to the rigidity of the connection, loosen them.

The invention also makes it possible to compensate for a further disadvantage which previously frequently occurred when several implants or their implant posts rising above the jaw ridge served as a fastening device for a removable denture. Previously, it was only rarely possible to align the implants so accurately that the forces occurring during chewing were transmitted uniformly to the individual implants. By using the fastening system according to the invention, this danger no longer exists, even when the two implants which are provided for receiving the ball-shaped supporting device are inserted in directions diverging from one another. The partially occurring rotation of the dentures on the ball heads has a compensating effect. It is also possible thereby to attach the ball heads on natural teeth, e.g., on individual lower corner teeth, rather than on implants. Great problems occurred here previously when these teeth stood in diverging directions and an accurate adaption of the construction to be inserted had to be carried out under the greatest difficulties.

An especially advantageous embodiment of the fastening system according to the present invention is that the ball heads are formed in such a way that their size is between about 55 and 90%, and preferably, between about 65 and 85% of the full spherical shape. As a result, the portion projecting into the mouth cavity is lower than with a full sphere so that parts going under one another can be avoided. This construction of the ball head also enables a better closure relative to an opening arranged in the jaw. Moreover, with this form of the ball head, a sufficiently large surface is always available for engagement with the retaining cap.

In a particularly preferred embodiment, the ball heads are produced from a dense sintered aluminum oxide with a purity of at least 97 weight percent since this material is biologically inert and there is no danger of dental tartar formation. Additionally, aluminum oxide is a preferred material for the production of the ball heads because it possesses a high resistance to wear and, in connection with a retaining cap produced from plastic, forms a friction pairing preferable for the object of the invention.

In particular, when the surface of the spherical heads is formed in such a way that it has a RMS value of $R_a < 0.2$ $\mu$m, the wear characteristics are reduced to a minimum and, moreover, especially good adherence between the ball heads and the retaining caps inserted in the denture is achieved.

In a preferred embodiment, the retaining caps are manufactured from polyvinyl chloride while the adapting rings are composed of polyethylene vinyl acetate. By means of this combination of materials, the retaining caps contact the ball heads in the area of their equators through the more elastic material of the adapting rings in a particularly advantageous manner, and thus provide for good adherence between the ball heads and the retaining caps fastened in the denture. This insures that the denture cannot rise off the ball head during normal horizontal and vertical loads.

Several possibilities are suitable for the fastening of the ball heads. For the fastening of the ball heads on an implant wherein enossal pin implants are especially preferred, it has proved especially advantageous to have a pin-shaped projection or shoulder on the ball heads. A thread for screwing the ball head on the implant can be optionally provided on its lower end. This type of fastening is especially advantageous because an exchange of the ball head can be effected in a relatively simple manner.

On the other hand, in order to secure a ball head with the help of a natural tooth root, a pin can be provided on the ball head having auxiliary retention means in the form of undulations, grooves, slots, notches, or undercuttings. This kind of auxiliary retention means ensures that a secure support of the pin or of the ball head with the newly forming bone web is achieved, particularly, when the pin is also made from non-sintered aluminum oxide as in another preferred embodiment.

The insertion and adaption of the fastening system according to the invention is described in the following example in which the ball heads are fastened on screw implants. In the same way, instead of the screw implants described here, other enossal implants or suitable natural teeth, in particular, singly standing lower corner teeth, can also be employed for attaching the ball heads according to the invention. The example relates to a denture for the tooth substitute of the lower jaw. The invention can also be applied in the upper jaw, however, there are particular advantages in application for the lower jaw area.

EXAMPLE

Two screw implants for fastening two ball heads are first inserted in a conventional manner in the toothless lower jaw. Subsequently, an impression is produced in the conventional manner with the help of a transmission system referred to herein as a place holder.

The place holders correspond approximately to the ball heads to be inserted later and are fastened with screws in openings provided in head parts of the implants projecting over the jaw. However, the outer contours of the place holders are different from the ball heads to the extent that their dimensions are increased by the wall thickness of the retaining cap and adapting ring. This place holder has the function of keeping the space in the denture, which will later be required for the insertion of the rotational cap and adapting ring, open. By means of this construction of the place holders, openings in the lower areas where the adapting rings will be attached are kept open in the denture which correspond exactly in their dimensions to the adapting rings. In the upper part, on the other hand, where the fastening of the retaining caps in the denture is effected by an adhesive and the dimensions of the place holders are likewise increased by the wall thickness of the adapting ring, the space which is required for inserting the adhesive is kept open by means of this measure. Any desired easily workable and inherently stable material can be employed as the material for producing the place holders. Brass, for example, has proved itself to be well suited.

After an impression has been made with the help of the place holder inserted in the implant, this place holder is removed from the implant and the opening in the implant is sealed until the insertion of the ball head. The place holder removed from the implants is inserted in the impression model and a denture is produced in a manner known per se after a positive model is made.

When the healing-in process of the implants is terminated after approximately 6 weeks, the seals are removed and the two ball heads made of dense-sintered aluminum oxide are inserted. This is effected by means of screwing in the pin-shaped projections which carry the ball head on one of their ends and have a thread on their other end. After the ball heads are fastened on the implants, the denture, manufactured in the meantime with the help of the impression, is placed on the ball heads. This denture contains the retaining caps which have already been securely glued in and the adapting rings enclosing the retaining caps.

We claim:

1. A fastening system for a removable mucous membrane-supported denture comprising:
    (a) two spherically shaped heads (1) fastened on implants or natural teeth, the heads (1) having a highly polished surface and a size exceeding hemispherical;
    (b) a mucous membrane-supported denture having two recesses (7) therein having walls (10) in that surface facing the mucous membrane;
    (c) two retaining caps (8) having openings (9) therein composed of a smooth elastic plastic material within said recesses (7) for engaging the heads and shaped for contacting the heads only in the area of their equator; and
    (d) adapting rings (12) composed of a plastic material which is more elastic than the material of the retaining caps (8) arranged between recess wall (10) and retaining caps (8) in the area of opening (9) of the retaining caps (8).

2. The fastening system of claim 1 wherein the shape of each heads (1) is between about 55% and 90% of the full sphere.

3. The fastening system of claim 1 wherein the ratio of the height (h) of adapting ring (12) to the radius (r) of the head (1) is between about 1:2.5 and 2:2.5.

4. The fastening system of claim 1, 2 or 3, wherein retaining cap (8) is fastened on wall (10) of recess (7) by a cold-polymerizable adhesive in such a way that at least the area (22) provided for the insertion of adapting ring (12) remains free of the adhesive.

5. The fastening system of claim 1, 2 or 3, wherein retaining cap (8) has a lower edge (23) which forms a flush closure with a lower edge (24) of said adapting ring (12).

6. The fastening system of claim 5, wherein wall (10) of recess (7) projects over the flushly closing lower edges (23, 24) of retaining cap (8) and adapting ring (12) by a distance (L) which is about 1/5 to 3/5 of the radius (r) of head (1).

7. The fastening system of claims 1, 2 or 3, wherein head (1) is composed of a densely sintered aluminum oxide having a purity of at least 97 weight percent.

8. The fastening system of claim 1, 2 or 3, wherein the surface of head (1) has a RMS value $R_a < 0.2$ μm.

9. The fastening system of claim 1, 2 or 3, wherein retaining cap (8) is composed of polyvinyl chloride.

10. The fastening system of claim 1, 2 or 3, wherein adapting ring (12) is composed of polyethylene vinyl acetate.

11. The fastening system of claim 1, 2 or 3, wherein head (1) has a pin (28) or a pin-shaped projection (2) composed of sintered aluminum oxide.

12. The fastening system of claim 1, 2 or 3, wherein head (1) has a conical pin-shaped projection (2) having an end (4) opposite head (1).

13. The fastening system of claim 1, 2 or 3, wherein head (1) has a cylindrical pin for securing said head (1).

14. The fastening system of claim 1, 2 or 3, wherein head (1) is arranged on a pin implant having a cylindrical shape.

* * * * *